(12) United States Patent
Kozioziemski et al.

(10) Patent No.: US 10,741,297 B2
(45) Date of Patent: Aug. 11, 2020

(54) 3-DIMENSIONAL X-RAY IMAGER

(71) Applicant: Lawrence Livermore National Security, LLC, Livermore, CA (US)

(72) Inventors: Bernard J. Kozioziemski, Livermore, CA (US); Nobuhiko Izumi, Oakland, CA (US); Julia K. Vogel, Pleasanton, CA (US); Louisa A. P. Pickworth, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 9 days.

(21) Appl. No.: 16/174,625

(22) Filed: Oct. 30, 2018

(65) Prior Publication Data
US 2019/0148029 A1 May 16, 2019

Related U.S. Application Data

(60) Provisional application No. 62/585,241, filed on Nov. 13, 2017.

(51) Int. Cl.
G21K 7/00 (2006.01)
G21K 1/06 (2006.01)
G01N 23/085 (2018.01)
A61B 6/02 (2006.01)

(52) U.S. Cl.
CPC .............. *G21K 1/062* (2013.01); *A61B 6/022* (2013.01); *G01N 23/085* (2018.02); *G21K 7/00* (2013.01); *G21K 2201/062* (2013.01)

(58) Field of Classification Search
CPC .... G21K 1/062; G21K 7/00; G21K 2201/062; G01N 23/085; A61B 6/022

USPC ............................................................ 378/43
See application file for complete search history.

(56) References Cited

U.S. PATENT DOCUMENTS

| 4,926,452 A | 5/1990 | Baker et al. |
| 2007/0071164 A1* | 3/2007 | Shu .................... G01N 23/2252 378/43 |

OTHER PUBLICATIONS

Bishop, "The Light Field Camera: Extended Depth of Field, Aliasing, and Superresolution," IEEE Transactions on Pattern Analysis and Machine Intelligence, vol. 34, No. 5, 2012, pp. 972-986.
Broxton et al., "Wave optics theory and 3-D deconvolution for the light field microscope," Optics Express, vol. 21, No. 21, 2013, pp. 25418-25439.
Helfen et al., "On the implementation of computed laminography using synchrotron radiation," Review of Scientific Instruments, vol. 82, 063702, 2011, 9 pp.
Kamilov et al., "Learning approach to optical tomography" Optica, vol. 2, No. 6, 2015, pp. 571-522.
Lu et al., "Imaging properties of extended depth of field microscopy through single-shot focus scanning," Optics Express, 2015, pp. 10714-10731.

(Continued)

*Primary Examiner* — Courtney D Thomas
(74) *Attorney, Agent, or Firm* — John P. Wooldridge

(57) ABSTRACT

The invention utilizes one exposure without moving parts to provide multiple x-ray views of an object. It relies on a 3D detector, which can be a stack of film plates, and a specified focusing x-ray optic. The x-ray optic, discussed below, allows collection of x-rays from a localized volume, just like an ordinary optical lens, and the stacked film plate, or other 3D detector design, allows collection of the multiple focal plane information from one line of sight.

26 Claims, 6 Drawing Sheets

(56) References Cited

OTHER PUBLICATIONS

Moore, "Three-Dimensional X-Ray Laminography as a Tool for Detection and Characterization of BGA Package Defects," IEEE Transactions on Components and Packaging Technologies, vol. 25, No. 2, 2002, pp. 224-229.
Ng et al., "Light Field Photography with a Hand-held Plenoptic Camera," Stanford Tech Report CTSR 2005-02, pp. 1-11.
Plantes, "Eine Neue Methode Zur Differenzierung in der Rontgenographie (Planigraphies)," Acta Radiologica, vol. 13, No. 2, 1932 pp. 182-192.
Schneberk et al., "Possible Laminographic and Tomosynthesis Applications for Wolter Microscope Scan Geometries," UCRL-TR-207196, 2004, 13 pp.
Sidky et al., "Image reconstruction in circular cone-beam computed tomography by constrained, total-variation minimization," Phys. Med. Biol., No. 53, 2008, pp. 4777-4807.
Suryanarayan et al., "Comparison of Tomosynthesis Methods Used with Digital Mammography," Academic Radiology, vol. 7, No. 12, 2000, pp. 1085-1097.
Tibbelin et al., "HyperSPECT: a New System for pre-clinical Imaging in vivo," Proc. of SPIE vol. 7258, 2009, 8 pp.
Tibbelin et al., "Simulation of HyperSPECT: a high-resolution small-animal system with in-line x-ray optics," Phys. Med. Biol., No. 57, 2012, pp. 1617-1629.

\* cited by examiner

3-DIMENSIONAL X-RAY IMAGER

CROSS-REFERENCE TO RELATED APPLICATIONS

This application claims the benefit of U.S. Provisional Patent Application No. 62/585,241 titled "3-Dimensional X-Ray Imager," filed Nov. 13, 2017, incorporated herein by reference.

STATEMENT AS TO RIGHTS TO INVENTIONS MADE UNDER FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC, for the operation of Lawrence Livermore National Laboratory.

BACKGROUND OF THE INVENTION

Field of the Invention

The present invention relates to x-ray imaging, and more specifically, it relates to x-ray imaging of 3D objects.

Description of Related Art

The technical problem is obtaining three-dimensional structural information inside of objects in a manner which is nondestructive. The most often applied approach is conventional computed tomography where either the object is rotated around one axis, or the x-ray source and detector are rotated around the object. The object structure is then determined using a computation algorithm. This limits the application to cases where the object and structure inside the object are not changing over the time period needed to perform the scan. Furthermore, the resolution is determined by the x-ray source and detector characteristics.

Schneberk, Jackson, and Martz suggested using a Wolter optic to acquire multiple images by scanning the Wolter optic and recording multiple images on a single CCD camera. The limitation is that the object must be stationary during the scan, and the translation of the optic needs to be done so as to not introduce additional artifacts. It is desirable to remove the time dependence from the imaging.

SUMMARY OF THE INVENTION

Wolter Type-I reflective x-ray mirrors have been used as optical components of x-ray microscopes. These microscopes have very short distances over which the image is in focus. This is generally a drawback in x-ray imaging because it limits the extent of an object which can be imaged. However, by combining this microscope with a three-dimensional detector, multiple in-focus images can be recorded that correspond to specific locations in the object. One implementation of a three-dimensional x-ray detector would be a stacked array of x-ray film or image plates. Each film or image plate partially absorbs the x-rays, thereby creating a recording of the x-ray intensity. Unabsorbed x-rays are partially transmitted to the next film or image plate. These multiple images allow a three-dimensional view of an extended object to be reconstructed computationally along one line of sight. Typical scales would have lateral resolution from 0.01 to 0.1 millimeter and depth resolution of 0.1-1 millimeter. By acquiring multiple images from a single line of sight with a 3D detector, the time dependence is removed from the imaging.

One use of the present invention is in imaging extended laser-produced x-ray sources, such as are produced in inertial confinement fusion experiments where high resolution and high throughput are required over an extended volume. Another use is in imaging objects that are small compared to the depth-of-field of a microscope, with the multiple views allowing one of the images to be in-focus. Another use is to obtain multiple slices of a large object. This can be applied to medical imaging to allow determination of the three-dimensional structure without the complication of rotating the x-ray source and detector used in typical computed tomography radiography. A single line-of-sight with the three-dimensional detector and short depth-of-focus optic allows individual slices to be reconstructed to better determine the shape and location of features. Additionally, other applications that require similar non-destructive evaluation would benefit from such technology. These include characterization of additively manufactured components. The invention finds uses in baggage screening and related applications. Additionally, this concept is applicable to other penetrating radiation that can be focused, such as low-energy neutrons.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The invention combines two different hardware pieces. The first is an x-ray optic with a depth-of-field that is small compared to the object under investigation. Reflective Wolter type x-ray optics are one such design. These hollow optics have a relatively large collection efficiency and can be designed with a large field of view. The depth of focus, which is the distance over which a feature can be resolved along the imaging direction, is relatively small for these optics; it is typically small compared to the field of view. These optics have been used extensively in x-ray astronomy and in some cases for x-ray microscopy. The short depth of field distance is often considered a drawback to the design. However, when combined with a three-dimensional x-ray detector, it is possible to take advantage of the short depth of field to obtain additional information about the 3D structure of an object. One simple version of the 3D detector uses film. The x-rays are partially transmitted and partially absorbed through a piece of x-ray. This allows the simultaneous recording of multiple images along one line of sight. This invention may take advantage of future developments in 3D x-ray detectors that might include thinned CCDs or CMOS detectors, or CCDs used with x-rays at energies that transmit well through the CCD.

In one embodiment, the Wolter optic portion is designed so that the depth of field is approximately $\frac{1}{10}^{th}$, of the object size, and ideally so that the resolution over a useable field of view is appropriate for the investigation. Short depth of field is achieved by making the ratio of the optic diameter to its focal length large. A typical value would be ~0.05 for these optics. The Wolter optic can be either designed for a broadband response, or a narrow band if a multilayer coating is employed on the optic surface.

Thus, it is now possible to use a single x-ray viewing axis to obtain 3D volumetric information from a sample. As discussed above, tomographic reconstructions typically require multiple x-ray images from different angles to determine the internal structure of an object. However, there are cases where constraints prohibit multiple views, either because the sample and detector cannot be rotated, or because the sample exists for a very short time, such as in ICF experiments. In the present invention, a focusing x-ray optic with a short depth-of-field, such as a Wolter style mirror, coupled with multiple partially transmitting detectors, allows for 3D interrogation with a single line of sight.

Figure 1:
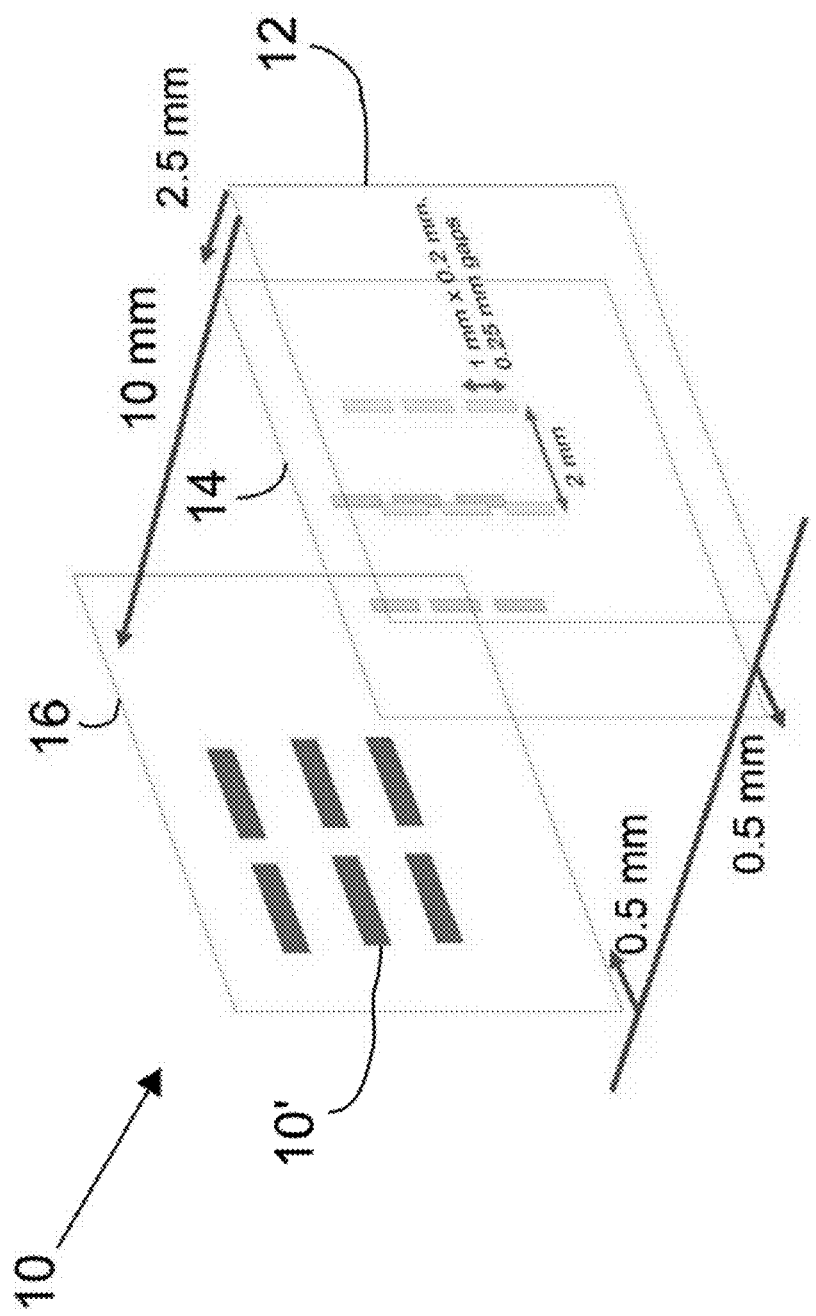
FIG. 1 illustrates an extended source of x-rays.

FIG. 1 illustrates an extended source of x-rays. The extended source 10 consists of six identical x-ray emitting bars at each of three different planes 12, 14 and 16. In this example, plane 14 is located 2.5 mm from plane 12 and plane 16 is located 10 mm from plane 12. Alternately, the bars can represent objects 10' casting shadows formed by x-ray illumination from behind plane 16 in the direction toward the other two planes. The 3 planes are offset one to another so that portions of the bars from one plane will not completely overlap the bars from the other planes. This allows the identification of the bars from a particular plane to be easily identified in any image collected downstream from the source. Plane 14 is offset 0.5 mm relative to plane 12 and plane 16 is offset 0.5 mm relative to plane 12 and in the opposite direction as the offset of plane 16.

Figure 2A:
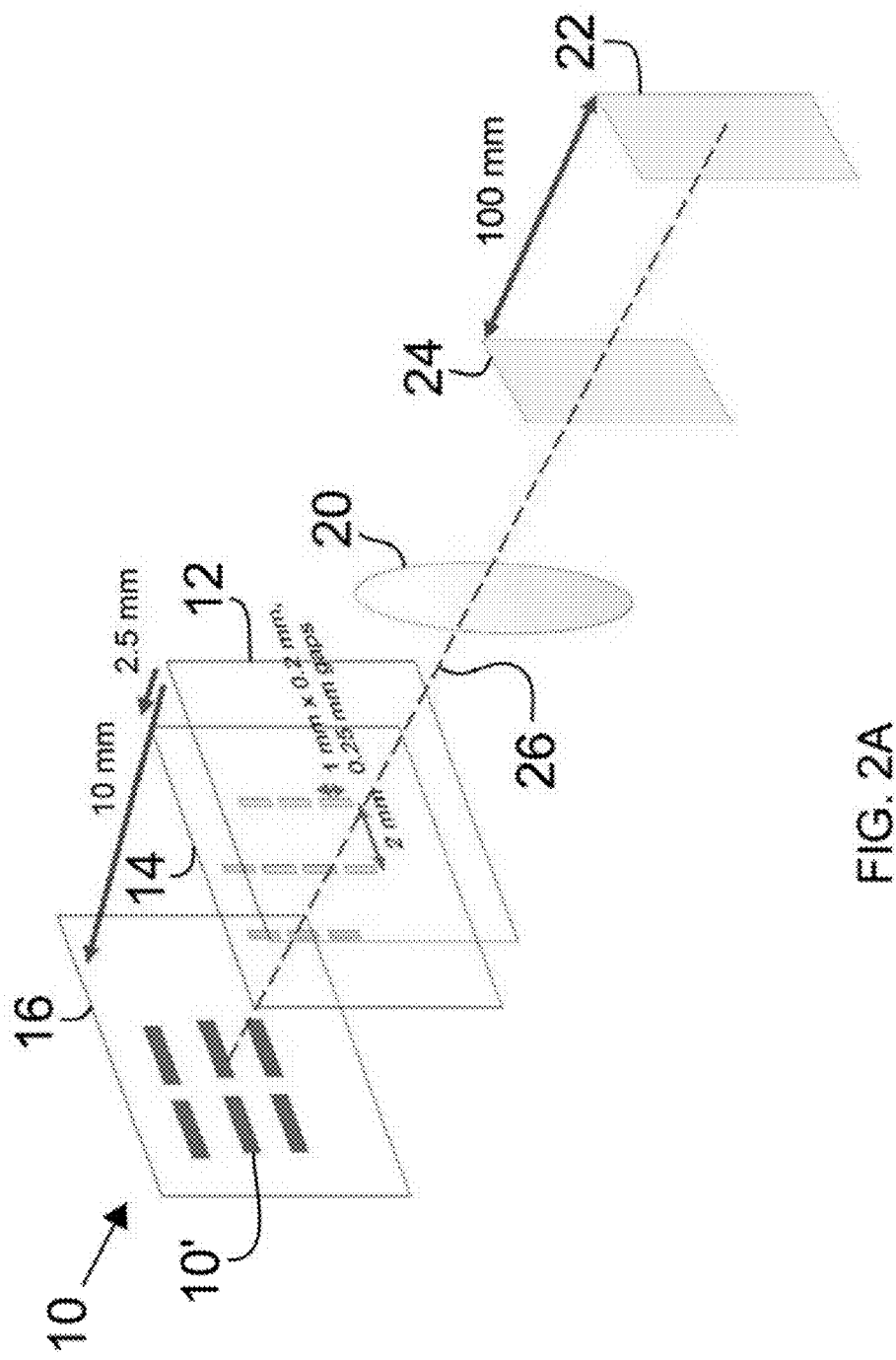
FIG. 2A shows a source and further includes a large depth of field x-ray optic and detectors all on optical axis.
Figure 2C:
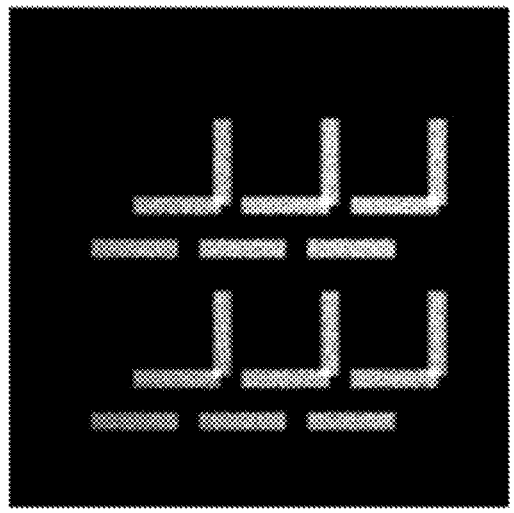
FIG. 2C shows the image collected at a second detector in the system of FIG. 2A.
Figure 2B:
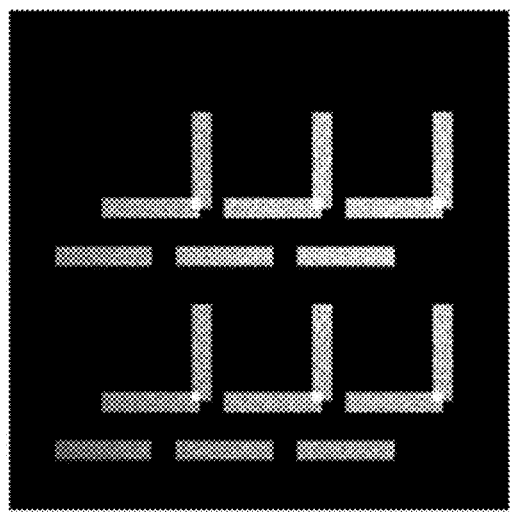
FIG. 2B shows the image collected at a first detector in the system of FIG. 2A.

This invention obtains three-dimensional structural information of an extended source or object. The source produces x-rays which emanate from different locations. FIG. 2A illustrates the problem this invention solves. An extended object, illuminated from behind by x-rays, would case shadows from the different object locations. FIG. 2A shows the source 10 (or objects 10') described above and includes a large depth of field x-ray optic 20 and detectors 22 and 24 all on optical axis 26. In this example, the detectors are separated by 100 mm. X-ray optic 20 has a large depth of field, which means that the ratio of the optic diameter to its focal length is small. The image from the source 10 slowly goes through focus, making it difficult to retrieve the 3D information. FIG. 2B shows the image collected at detector 24. FIG. 2C shows the image collected at detector 22. Notice that the image of the bars from the 3 planes are nearly identical and that all of the bars are in focus. Thus, an optic with a large depth of field cannot provide depth information, even with a 3D detector, or two separated detectors.

Figure 3A:
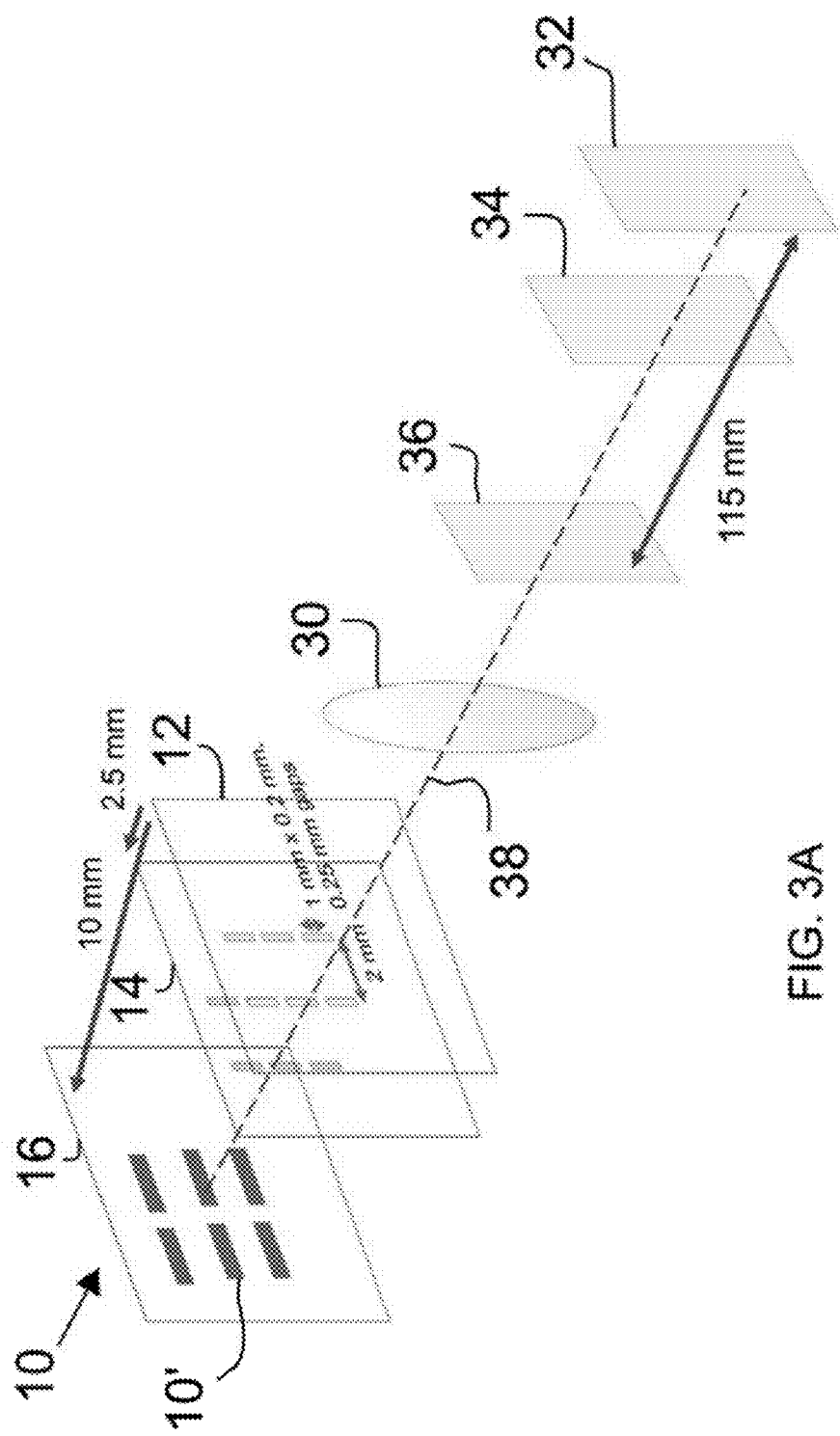
FIG. 3A illustrates an embodiment of the present invention and includes a source, a short depth of field x-ray optic and detectors all on an optical axis.
Figure 3D:
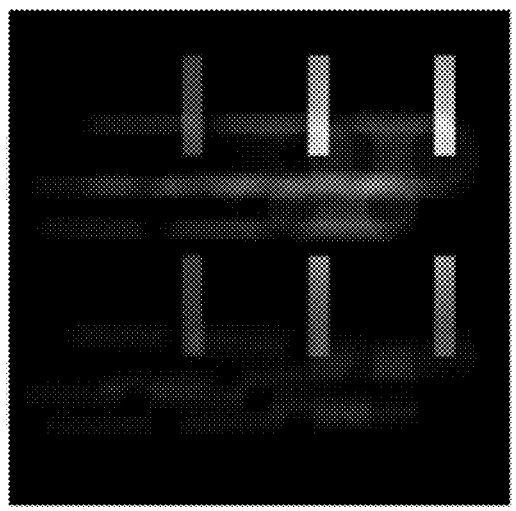
FIG. 3D shows the image from a third detector plane of FIG. 3A.
Figure 3C:
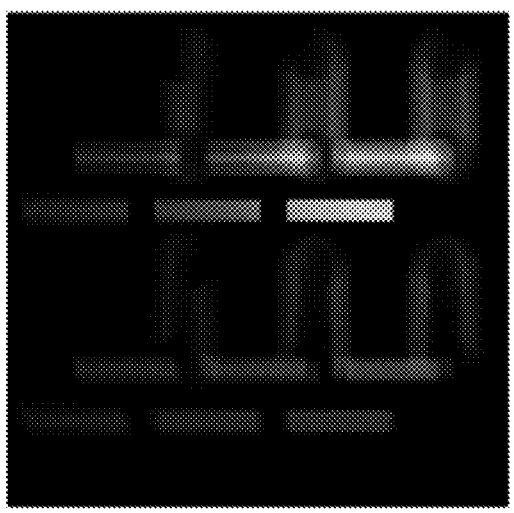
FIG. 3C shows the image from a second detector plane of FIG. 3A.
Figure 3B:
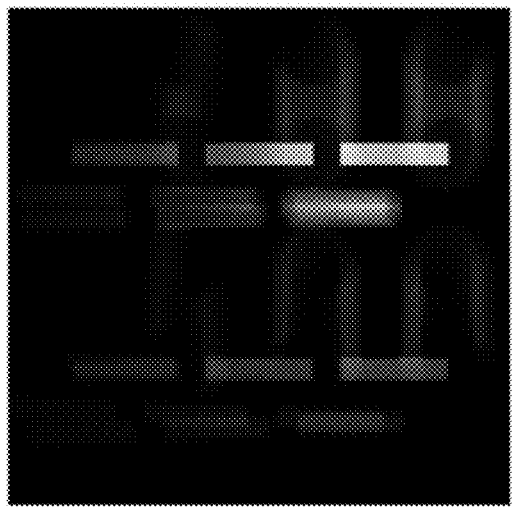
FIG. 3B shows the image from a first detector plane of FIG. 3A.

FIG. 3A illustrates an embodiment of the present invention. The figure includes the same extended source 10 or objects 10' shown on FIG. 1 and FIG. 2A. An x-ray optic 30 and detectors 32, 34 and 36 are shown on optical axis 38. In this example, detectors 32 and 36 are separated by 115 mm. X-ray optic 30 has a short depth of field, which means that the ratio of the optic diameter to its focal length is large. The image from the source 10 (or planes 12, 14 and 16) is therefore focused at different planes. The image of plane 12 is focused on detector 32. The image of plane 14 is focused onto detector 34 and the image of plane 16 is focused onto detector 36. In other words, the detectors 32, 34 and 36 are placed so that they are at the position where optic 30 focuses the respective planes 12, 14 and 16. FIG. 3B shows the image from plane 12 collected at detector 32. FIG. 3C shows the image from plane 14 collected at detector 34. FIG. 3D shows the image from plane 16 collected at detector 36. Notice that the image of the bars from only a single plane are in focus at their respective detector. The offsets of the planes, as described above, are apparent in the respective images. Thus, an x-ray optic with a short depth of field can provide depth information with a 3D detector, or separated detectors (3 detectors in this case).

As mentioned above, it is necessary that the image plates (detectors) are partially transmissive for the x-ray energies used in a particular embodiment. Generally, image plates are partially transmissive over a wide range of x-ray energies. Example image plate density and composition are shown in the table below, which is from A. L. Meadowcroft, et al., Rev. Sci. Inst. 79 113102 (2008).

TABLE 1

| Fuji BAS image plate material specifications | | | | | | |
|---|---|---|---|---|---|---|
| | Mylar layer | | | Phosphor layer | | |
| IP type | Composition | Density (g/cm$^3$) | Thickness (μm) | Composition | Density (g/cm$^3$) | Thickness (μm) |
| SR | $C_{10}H_8O_4$ | 1.49 | 8 | BaFBr | 3.07 | 112 |
| TR | | None | | $BaFB2_{0.85}I_{0.15}$ | 2.61 | 60 |
| MS | $C_{10}H_8O_4$ | 1.64 | 9 | $BaFB2_{0.85}I_{0.15}$ | 3.18 | 124 |

Figure 4:
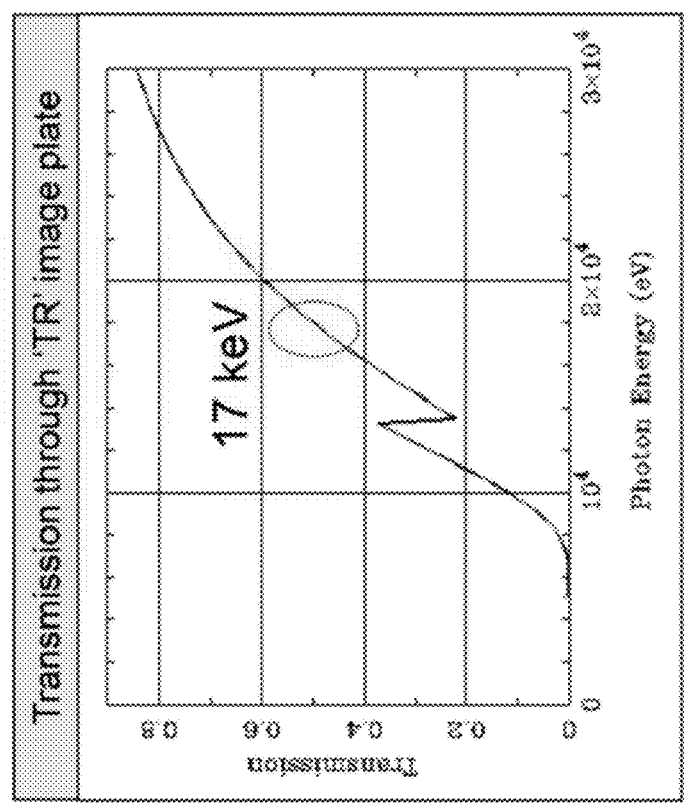
FIG. 4 shows x-ray transmission through a TR image plate.

Transmission through a TR image plate is shown in FIG. 4. Notice that the TR image plate has about 50% transmission at 17 keV (Mo K-alpha line). Ideally, transmission >50% would balance intensity on successive image plates. Transmission can in principle be tuned for different energies, with a change in phosphor layer thickness. Based on the teachings herein, those skilled in the art will recognize other methods to construct a multi-plane detector useable in the present invention. Multiple detectors including stacked CCD or CMOS detectors, may also be used in the invention. This concept can be applied to other penetrating radiation systems such as low-energy neutrons and high energy electrons.

Some embodiments utilize a back-propagation or similar computational algorithm to take full advantage of the data. The known detector positions allow such a numerical computation of the object under study. One exemplary computation uses the general steps described below.

Step 1: Measure distance between optic and first detector, optic and second detector.

Step 2: Collect data on first detector (I1) and second detector (I2).

Step 3: Compute the mean of the data from the first and second detectors, A1.

Step 4: Subtract the mean data, A1, from first detector data and the second detector data. Features out of focus for both detectors will not change significantly and will not appear in the difference images, D1 and D2.

Step 5: D1 represents the structures nearly in focus (S1) for the first detector, D2 represents the structure nearly in focus for the second detector (S2). The location of these structures in the three-dimensional object is obtained using the known optic focal length and the distance between optic and first detector and optic and second detector.

Step 6: Use a raytracing or beam-propagation algorithm to produce a best match to S1 and S2 based on a computer model of the three-dimensional object, M1 and M2.

Step 7: Generate a simulated images SI1 and SI2 from M1 and M2 using the optic focal length and measured distance from the optic to the first detector and the optic to the second detector.

Step 8: Subtract SI1 from I1 and SI2 from I2 to produce residual images R1 and R2.

Step 9: Back-propagate the residual images through the optic using raytracing or beam propagation and determine where the rays would have originated from in the object, SI3.

Step 10: Generate a computer model, M3, from SI3 using raytracing or beam propagation. Update three-dimensional object model to now include M1, M2, and M3.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. A method, comprising:
   directing a single exposure of penetrating radiation onto a first object and then onto a second object to produce a first shadow of said first object and a second shadow of said second object;
   collecting said first shadow and said second shadow with an optic, wherein said optic is configured to redirect said first shadow and said second shadow;
   detecting said first shadow with a first detector, wherein said first detector produces a first signal corresponding to said first shadow;
   detecting said second shadow with a second detector, wherein said second detector produces a second signal corresponding to said second shadow; and
   using said first signal and said second signal to determine the relative locations of said first object and said second object.

2. The method of claim 1, wherein said penetrating radiation comprises x-rays.

3. The method of claim 1, wherein said penetrating radiation comprises low-energy neutrons.

4. The method of claim 1, wherein said optic is configured to focus said first shadow at a first image plane and to focus said second shadow at a second image plane.

5. The method of claim 4, wherein said first shadow will not be in focus at said second image plane and wherein said second shadow will not be in focus at said first image plane.

6. The method of claim 1, wherein said optic comprises an x-ray optic.

7. The method of claim 1, wherein said optic comprises a depth-of-field that is small compared to the size of said first object and said second object.

8. The method of claim 1, wherein said optic comprises a depth-of-field that is less than $\frac{1}{10}^{th}$ of the size of said first object and said second object.

9. The method of claim 1, wherein said optic is a Wolter optic.

10. The method of claim 1, wherein said optic is selected from the group consisting of a bent crystal optic and a Fresnel zone plate.

11. The method of claim 1, wherein at least one of said first detector and said second detector comprises x-ray film.

12. The method of claim 1, wherein at least one of said first detector and said second detector comprises an image plate.

13. An apparatus, comprising:
   a source of penetrating radiation configured for directing a single exposure of said penetrating radiation onto a first object and then onto a second object to produce a first shadow of said first object and a second shadow of said second object;
   an optic positioned for collecting said first shadow and said second shadow, wherein said optic is configured to redirect said first shadow and said second shadow, wherein said optic comprises a depth-of-field that is small compared to the size of said first object and said second object;
   a first detector configured for detecting said first shadow; and
   a second detector configured for detecting said second shadow.

14. The apparatus of claim 13, wherein said penetrating radiation comprises x-rays.

15. The apparatus of claim 13, wherein said penetrating radiation comprises low-energy neutrons.

16. The apparatus of claim 13, wherein said optic is configured to focus said first shadow at a first image plane and to focus said second shadow at a second image plane.

17. The apparatus of claim 16, wherein said first shadow will not be in focus at said second image plane and wherein said second shadow will not be in focus at said first image plane.

18. The apparatus of claim 13, wherein said first detector is configured to produce a first signal corresponding to said first shadow and said second detector is configured to produce a second signal corresponding to said second shadow.

19. The apparatus of claim 13, wherein said optic comprises an x-ray optic.

20. The apparatus of claim 13, wherein said optic comprises a depth-of-field that is less than $\frac{1}{10}^{th}$ of the size of said first object and said second object.

21. The apparatus of claim 13, wherein said optic is a Wolter optic.

22. The apparatus of claim 13, wherein said optic is selected from the group consisting of a bent crystal optic and a Fresnel zone plate.

23. The apparatus of claim 13, wherein at least one of said first detector and said second detector comprises x-ray film.

24. The apparatus of claim 13, wherein at least one of said first detector and said second detector comprises an image plate.

25. A method, comprising:
   simultaneously collecting, with an optic, first penetrating radiation from a first source and second penetrating radiation from a second source, wherein said optic is configured to redirect said first penetrating radiation and said second penetrating radiation to produce first redirected rays and second redirected ray, respectively;

detecting said first redirected rays with a first detector, wherein said first detector produces a first signal corresponding to said first shadow;

detecting said second redirected rays with a second detector, wherein said second detector produces a second signal corresponding to said second shadow; and using said first signal and said second signal to determine the relative locations of a first object and a second object.

26. A method, comprising:

simultaneously collecting, with an optic, first penetrating radiation from a first location and second penetrating radiation from a second location, wherein said first location and said second location are different distances from said optic, wherein said optic is configured to redirect said first penetrating radiation and said second penetrating radiation to produce first redirected rays and second redirected ray, respectively;

detecting said first redirected rays with a first detector, wherein said first detector produces a first signal corresponding to said first shadow;

detecting said second redirected rays with a second detector, wherein said second detector produces a second signal corresponding to said second shadow; and using said first signal and said second signal to determine the relative locations of a first object and a second object.

\* \* \* \* \*